United States Patent
Hegele-Hartung et al.

(10) Patent No.: US 6,794,409 B2
(45) Date of Patent: Sep. 21, 2004

(54) USE OF ERβ-SELECTIVE LIGANDS FOR REGULATING FERTILITY AND COMPOUNDS USEFUL THEREFOR

(75) Inventors: Christa Hegele-Hartung, Muelheim a.d. Ruhr (DE); Karl-Heinrich Fritzemeier, Berlin (DE); Hiroshi Yamanouchi, Berlin (DE); Olaf Peters, Jena (DE); Dirk Kosemund, Erfurt (DE); Gerd Mueller, Jena (DE); Ingo Tornus, Henningsdorf (DE); Gerd Schubert, Jena (DE); Sven Ring, Jena (DE)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 10/083,685

(22) Filed: Feb. 27, 2002

(65) Prior Publication Data

US 2003/0083377 A1 May 1, 2003

Related U.S. Application Data

(60) Provisional application No. 60/271,409, filed on Feb. 27, 2001, and provisional application No. 60/329,736, filed on Oct. 18, 2001.

(30) Foreign Application Priority Data

Oct. 17, 2001 (DE) .......................................... 101 51 365

(51) Int. Cl.$^7$ ................... A61K 31/215; A61K 31/075; C07C 69/02; C07C 43/20
(52) U.S. Cl. ....................... 514/510; 514/718; 560/231; 568/663; 568/715; 552/626
(58) Field of Search ................. 568/663, 715; 560/231; 514/510, 718; 552/626

(56) References Cited

U.S. PATENT DOCUMENTS

4,578,475 A 3/1986 Fürst et al.

FOREIGN PATENT DOCUMENTS

| WO | WO 00/47603 A2 | 8/2000 |
| WO | WO 00/63228 A1 | 10/2000 |

OTHER PUBLICATIONS

Labrie et al., "EM–652 (SCH 57068), a third generation SERM acting as pure antiestrogen in the mammary gland and endometrium," *Journal of Steroid Biochemistry and Molecular Biology*, 69 (1999), pp. 51–84.

Lotz, "Biological activities and receptor affinities of some natural and synthetic oestrogens and their D–homo analogues," *Experientia*, pp. 1373–1374, XP–002228748, 1978.

Katzenellenbogen, "Exploring The Structural Space Of Estrogen Receptor Ligands: Subtype–Selective Binding And Activation," *Abstracts of Papers American Chemical Society*, vol. 222, No. 1–2, 2001, p. 86, XP–008012796.

*Primary Examiner*—Barbara P. Badio
(74) *Attorney, Agent, or Firm*—Millen, White, Zelano & Branigan, P.C.

(57) ABSTRACT

The present invention discloses the use of ERβ-selective ligands for production of medicaments for regulating fertility without additional use of a progestin.

ERβ-agonists are used for treatment of infertility and ERβ-antagonists for contraception.

27 Claims, 3 Drawing Sheets

USE OF ERβ-SELECTIVE LIGANDS FOR REGULATING FERTILITY AND COMPOUNDS USEFUL THEREFOR

This application claims the benefit of the filing date of German Application No. 101 51 365.8 filed Oct. 17, 2001 and U.S. Provisional Applications Ser. Nos. 60/271,409 filed Feb. 27, 2001 and 60/329,736 filed Oct. 18, 2001.

FIELD OF INVENTION

The present invention relates to the use of a new principle for (a) improving pregnancy potential with ERβ-agonists in connection with in vivo treatment and in connection with in vitro fertilisation (IVF) and embryo transfer treatment and (b) inhibiting pregnancy potential with ERβ-antagonists. More specifically, the application relates to (a) improvement of pregnancy potential of oocytes and preimplantational embryos by improvement and stimulation of ovarian folliculogenesis and (b) inhibition of pregnancy potential by inhibiting folliculogenesis, ovulation and preimplantational development of ovulated oocytes.

This present invention relates further to new compounds as pharmaceutical active ingredients, which have in vitro a higher affinity to estrogen receptor preparations of rat prostates than to estrogen receptor preparations of rat uteri and exert a contraceptive action in vivo by their preferential action on the ovary, to their production, their therapeutic application and pharmaceutical forms for dispensing that contain the new compounds.

The chemical compounds are novel, steroidal, tissue-selective antiestrogens.

BACKGROUND OF THE INVENTION

Follicular growth refers to the development of an ovarian follicle from the primordial to antral follicle. Patients suffering from ovarian infertility, e.g. polycystic ovarian syndrom patients, have a disordered folliculogenesis and the numbers of primary and secondary follicles are about twice those observed in the normal ovary (Hughesden (1982), Obstet Gynecol Survey 37:59–77). Therefore, it may be concluded that follicular growth is often impaired in infertility patients.

There is evidence that most, if not all, of the steps from primordial to early antral follicles are gonadotropin-independent but it is not yet clear which of the many candidates among the paracrine and autocrine factors which have been identified in preantral follicles are the most important for early follicular growth (Elvin et al. (1999), Mol Cell Endocrinol 13:1035–1048; McNatty et al. (1999), J Reprod Fertil Suppl 54:3–16). Gonadotropins are mainly involved for the late steps of folliculogenesis, e.g. the transition from an early antral follicle to an ovulatory follicle.

Couples seeking infertility treatment will often be subject to different in vivo and in vitro treatment regimes. In vitro and vivo infertility (IVF) treatment regimens often consists of ovulation induction by pretreatment with exogenous gonadotrophins, mainly follicle stimulating hormone (FSH) and antiestrogens (White et al. (1996), J Clin Endocrinol Metab 81:3821–3824). The in vitro treatment protocol then involves retrieving the oocytes from the preovulatory, antral follicles of the ovaries in order to be matured and/or fertilised in vitro. After fertilisation and preimplantational embryo development, one to three embryos are retransfered in the woman's uterus in order to get a successful pregnancy. IVF is now an established treatment, which has been performed on a large scale for more than 20 years.

The protocols used for administration of exogenous gonadotropins are numerous and not without risks and disadvantages. The major disadvantages includes the risk of achieving ovarian hyperstimulation syndrome (OHSS) which in severe cases may be life threatening, the economic costs to the couple, side effects from the gonadotropin preparations including weight gain, bloating, nausea, vomiting, and the unknown long-term cancer risk.

One way to alleviate the risks, side effects, and economic disadvantages of controlled ovarian stimulation protocols would be to properly mature and stimulate follicular growth of ovarian infertility patients in vivo with a suitable agent before exogenous gonadotropin treatment starts. This approach would imply that the women are without gonadotropin stimulation or receive a minimal exogenous gonadotropin stimulation.

On the other hand contraceptive methods involving the administration of chemical substances are widely practiced among women who desire to limit pregnancies. Among the presently used chemical methods of fertility control, the most important are those which act by means of the following:

(a) suppression of ovulation through inhibition of gonadotropin release (inhibition of the endocrine principle), (b) alteration of the female reproductive tract to prevent migration of sperm to the site of fertilisation, (c) blocking the implantation of the zygote (nidation), (d) spermicidal action or (e) an abortifacient.

The oral contraceptives, consisting of an estrogen combined with a progestin or a progestin alone, are the most prominent chemical contraceptive agents. The contraceptives of the combined type act primarily by suppressing ovulation by negative feedback to prevent gonadotropin release by the pituitary. Although the oral contraceptives are highly effective, their use is associated with unpleasant side effects, such as nausea, depression, weight gain and headache, and an increased long-time risk of severe disease, such as thromboembolism, stroke, hepatic adenoma, gall bladder disease, hypertension and bleeding irregularities, indicating that an effective contraceptive principle without sides effects is presently not available. Therefore a need exists in medicine for new contraceptive methods.

An ideal contraceptive compound acting on the ovarian follicle would be an agent that does not modify the endocrine pituitary—ovarian communication system but selectively interrupt folliculogenesis, e.g. the paracrine interplay between the granulosa cell and the oocyte, leading (a) to an impairment of the follicular programm and an ovulated oocyte that is uncapable to get fertilised or (b) to an impairment of the follicular programm and an inhibition of ovulation, Follicular growth is the development of an ovarian follicle from the primordial stage to the large antral follicle that is ready to burst. Only an optimally built-up antral follicle has the potential to ovulate a mature egg cell. Patients with ovarian infertility, e.g., PCOS (=polycystic ovarian syndrome) patients, have a disrupted folliculogenesis associated with hormonal and ovulation disorders as well as insufficiently matured egg cells (Franks et al. (2000) Mol Cell Endocrinol 163:49–52).

There are always more indications that the early stages of folliculogenesis, i.e., the development steps from the primordial follicle to the early antral follicle, are gonadotrophin-independent, but it is still not conclusively explained which of the identified autocrine or paracrine factors (Elvin et al. (1999). Mol Cell Endocrinol 13:1035–1048; McNatty et al. (1999), J Reprod Fertil Suppl 54; 3–16) are the most important in early folliculogenesis. Gonadotrophins, such as, e.g., FSH (follicle-stimulating hormone), however, are mainly involved in the late steps of folliculogenesis, i.e., the development from the early antral follicle to the large ovulatory follicle. Additional modulators of folliculogenesis are also discussed in the late folliculogenesis, however (Elvin et al. (1999), Mol Cell Endocrinol 13:1035–1048).

Until recently, only a single type of estrogen receptor (ER) has thought to exist and mediate the genomic effects of 17β-estradiol in mammalian tissues. However, the cloning of a gene encoding a second type of ER, termed ERβ has prompted a reevaluation of estrogen actions (Kuiper et al (1996), Proc Natl Acad Sci 93:5925–5930). Whereas transcripts encoding the classical ER (now referred to as ERα) are detected in nearly all tissues assayed from both sexes in animal models, the highest expression of ERβ mRNA can be observed in the ovary (Couse et al. (1997), Endocrinology 138:4613–4612). Because ERα and ERβ have different tissue distributions, especially regarding the ovary, differences in ligand interaction or activity with the two ERs could translate into important differences in their biological actions at the tissue level. After the successful generation of ERα and ERβ knockout mice (Couse et al. (1999), Endocrine Reviews 20:358–417) it is now known that ERα and ERβ mediate different actions in the female reproductive tract and that ERα plays an important role in the function of the adult uterus, the mammary gland, in the negative regulation of gonadotropin action, whereas ERβ is mainly involved in ovarian physiology.

ERα and ERβ have significantly different primary sequences in their ligand binding and transactivation domains. This suggests that these ER subtypes might bind some ligands with different affinity and that these ligands might also have different agonist or antagonist character mediated by the two receptors.

Recent patent applications (WO 00/47503, WO 00/63228, PCT/EP00/10804, DE 100 19 167.3 and U.S. 60/207,370) and publications (Sun et al. (1999), Endocrinology 140:800–804; Stauffer et al. (2000), J Comb Chem 2:318–329) showed that high-affinity steroidal and nonsteroidal ligands for the ERα and ERβ were found. Some compounds were considerably more potent as agonists/antagonists on the ERα where others were considerably more potent as agonists/antagonists on the ERβ. In WO 00/31112 new steroid compounds based on estradiol and carrying a hydrocarbon as 11β-substitution which has one single linear chain having a length of from 5 to 9 carbon atoms. The compounds have an ERα-agonist/ERβ-antagonist profile. The mixed estrogen-receptor profile makes these compounds suitable as improved estrogens for treatment of estrogen-related disorders and in contraception together with a progestogen.

All above mentioned applications and publications are incorporated herein by reference However, so far a selective action of ER subtype-specific interaction in vivo could not be shown.

The present invention shows for the first time the effects of ERβ agonists/antagonists in defined animal models. The data obtained are the first showing that ERβ subtype-specific compounds are useful in defining biological activities in the ovary. From these data it becomes evident that ERβ plays an important role in (a) early folliculogenesis and (b) ovulation which can be taken as a new principle for treatment of infertility and the design of new contraceptives.

The following examples serve for explaining the invention without limiting the invention to these examples.

EXAMPLES

Example 1

Effect of an ERβ-selective Ligand on Folliculogenesis in Hypophysectomized Rats

Intact immature female Wistar rats were hypophysectomized (hypex) on day 24 of age (d0). The following hormone treatments were initiated six days after surgery:

(a) hypex rats treated with vehicle (control group) (ethanol/arachisoil: 1+9 [v/v]) only (b) hypex rats treated with 0.01, 0.1 and 1 mg 17β-estradiol/day (compound A)

(c) hypex rats treated with 0.01, 0.1 and 1 mg of an ERα-selective, 3,17β-Dihydroxy-19-nor-17α-pregna-1,3,5(10)-triene-21,16α-lactone (compound B, DE 100 48 634.7);

(d) hypex rats treated with 0.01, 0.1 and 1 mg of an ERβ-selective compound #1,8β-Vinyl-1,3,5(10)-estratriene-3,17β-diol (compound C, DE 100 19 167.3/U.S. 60/207,370);

(e) hypex rats treated with 0.01, 0.1 and 1 mg of an ERβ-selective compound #2 (16a-Hydroxy-9a-methyl-estra-1,3,5(10)-triene, compound D).

Animals were subcutaneously treated once per day for 4 consecutive days with the respective compounds or vehicle (day 6, 7, 8, 9). Number of animals per group were 5–6. The animals were randomly assigned to the treatment and vehicle (control) group.

One day after the last injection (day 10) animals were weighed and sacrificed by carbon dioxide asphyxiation. The ovaries were excised and weighed. Relative ovarian weights (in milligrams), defined as relative ovarian wet weights, were calculated per 100 g body weight for each animal. For each treatment group and control group the mean relative wet weights were determined. The one way ANOVA was applied to the data in order to compare treatment group values with the respective control group.

For histological evaluation, ovaries were placed in neutral buffered 3.7% formaldehyde solution. The ovaries were then embedded in paraffin, cut into 4 μm transverse sections, and stained with hematoxylin and eosin. Ovarian sections were then evaluated qualitatively for folliculogenesis.

Figure 1:
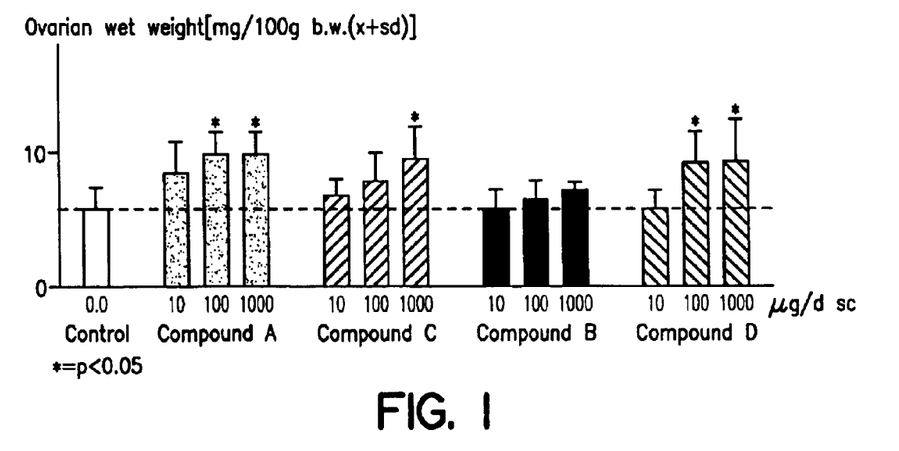
FIG. 1 shows the influence of ERα- and ERβ- selective ligands on ovarian wet weight in Hypex immature Wistar rats.

The results presented in FIG. 1 demonstrate that 17β-estradiol, which is a ligand to ERα as well as to ERβ, and both ERβ-specific ligands dose-dependently are able to significantly increase ovarian wet weight. In contrast, the ERα-specific ligand was not able to stimulate ovarian growth.

Figure 2:
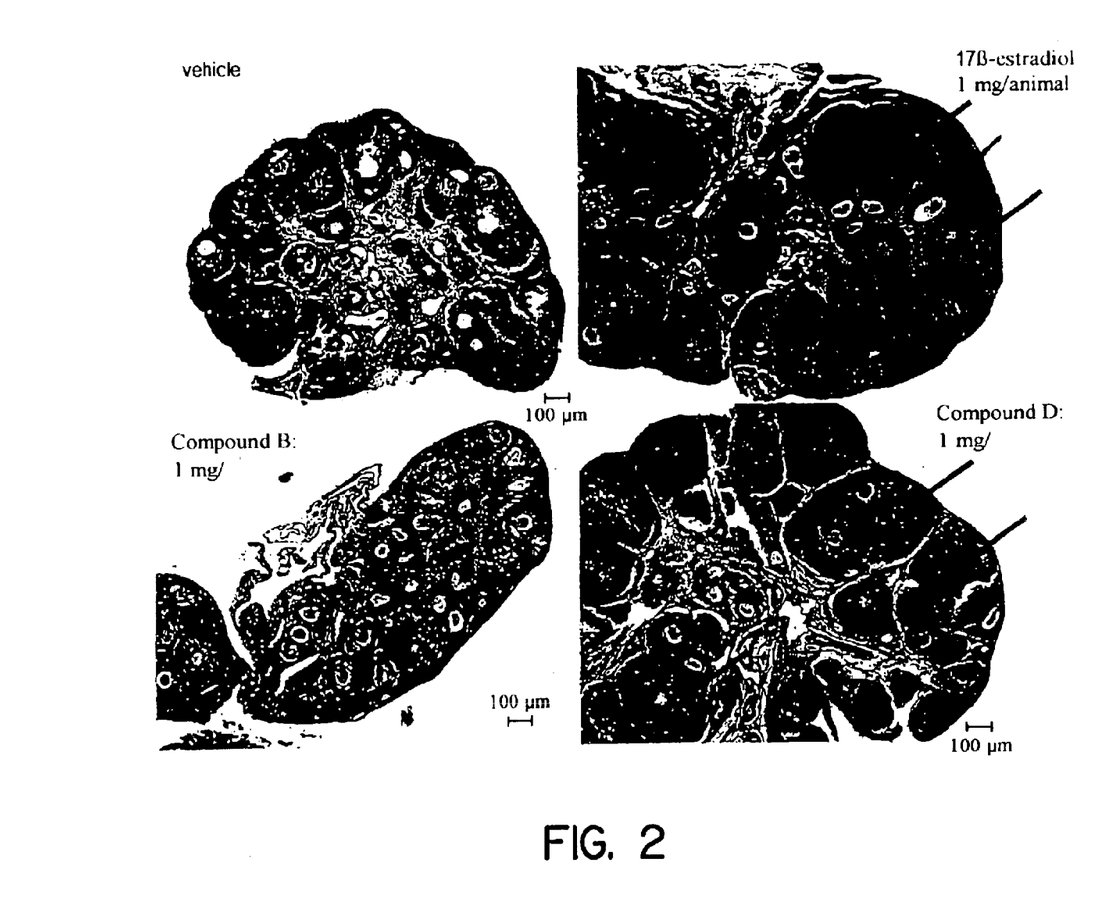
FIG. 2 shows the influence of ERα- and ERβ- selective ligands on folliculogenesis in Hypex immature Wistar rats. The histological sections were stained with hematoylin and eosin, of ovaries treated with vehicle, 17β-estradiol, ERα-selective ligand (compound B) and an ERfβ-selective ligand (compound D). The arrows indicate large preantral follicles.

The histological data presented in FIG. 2 clearly demonstrate that, compared to control animals, the increase in ovarian weight after treatment with 17β-estradiol and the ERβ-specific ligands are due to an enlargement in follicular size. Only a few small follicles are found. After treatment with the ERα-specific ligand the ovaries exhibit many small atretic follicles comparable to the vehicle control group.

Example 2
Effect of an ERβ-selective Antagonist an Ovulation Rate in Immature Rat Superovulation experiments were carried out in three groups of intact immature female Wistar rats on day 23 of age. Number of animals per group were 5. The animals were randomly assigned to the three groups.

Each animal received a single subcutaneous (s.c.) injection of 20 I.U. pregnant mare's serum gonadotropin (PMSG) at day 0. At the same time (day 0) as well as 24 hours and 48 hours later the animals were s.c. injected with (a) the vehicle formulation (control group: ethanol/aracisoil: 1+9 [v/v]) (group 1) or (b) an ERβ- selective antagonist 17-Chloro-17aα-(trifluoromethyl)-17a-homoestra-1,3,5(10)16-tetraene-3,17aβ-diol (compound E) at the dose of 1 mg/kg (group 2) and 10 mg/kg (group 3). 54 hours after the start of the experiment the animals got a single intraperitoneal (i.p.) injection of 10 I.U. human chorion gonadotropin (hCG). The animals were then killed 16 hours after the hCG injection.

The ovaries and oviducts were removed. The ovulated oocyte/cumulus mass was extracted from the oviduct by flushing the oviduct with M-2 medium and the oocytes per animal were counted after enzymatic disassociation from the surrounding cumulus with M-2 medium supplemented with 0.3% hyaluronidase.

The results presented in Table 1 demonstrate that the ERβ-specific antagonist was dose-dependently able to decrease ovulation rate from 13.2 in the group 1 (control) to 8.0 in group 3.

TABLE 1

Oocyte yield after superovulation of immature Wistar rats

| Group | Treatment (/day) × 3 days | Animal number | Ovulation rate (ova/rat) [x ± sd] |
|---|---|---|---|
| 1 | Vehicle | 5 | 13.2 ± 7.9 |
| 2 | 1 mg/kg compound E | 5 | 11 ± 5.6 |
| 3 | 10 mg/kg compound E | 5 | 8 ± 7.2 |

Example 3
Effect of an ERβ-selective Ligand on Late Folliculogenesis and Ovulation in Hypophysectomized Rats Intact immature female Wistar rats were hypophysectomized (hypex) on day 24 of age (day 0). The following hormone treatments were initiated six days after surgery:

(a) hypex rats treated with vehicle (control group) (ethanol/arachisoil: 1+9 [v/v]) only (b) hypex rats treated with 0.01, 0.1 and 1 mg 17β-estradiol/day (c) hypex rats treated with 0.01, 0.1 and 1 mg of the ERα-selective compound B (d) hypex rats treated with 0.01, 0.1 and 1 mg of the ERR-selective compound C Animals were subcutaneously treated once per day for 4 consecutive days with the respective compounds or vehicle (day 6, 7, 8, 9). Number of animals per group were 57. The animals were randomly assigned to the treatment and vehicle (control) group.

One day after the last injection (day 10) animals were subcutaneously injected with 20 IU prgenant mare serum gonadotropin (PMSG). Two days later, at day 13, 10 IU human Chorionic Gonadotropin (hCG) were injected intraperitoneally in order to induce ovulation. At day 14 animals were weighed and sacrificed by carbon dioxide asphyxiation. The oviducts and ovaries were removed:

The oviducts were flushed with a M-2 medium and the oocytes per animal were counted after enzymatic disassociation from the surrounding cumulus with M-2 medium supplemented with 0.3% hyaluironidase. For each treatment group and control group the mean number of ovulated oocytes were calculated.

The ovaries were excised and weighed. Relative ovarian weights (in milligrams), defined as relative ovarian wet weights, were calculated per 100 g body weight for each animal. For each treatment group and control group the mean relativewet weights were determined.

The one way ANOVA was applied to the data in order to compare treatment group values with the respective control group.

Figure 3:
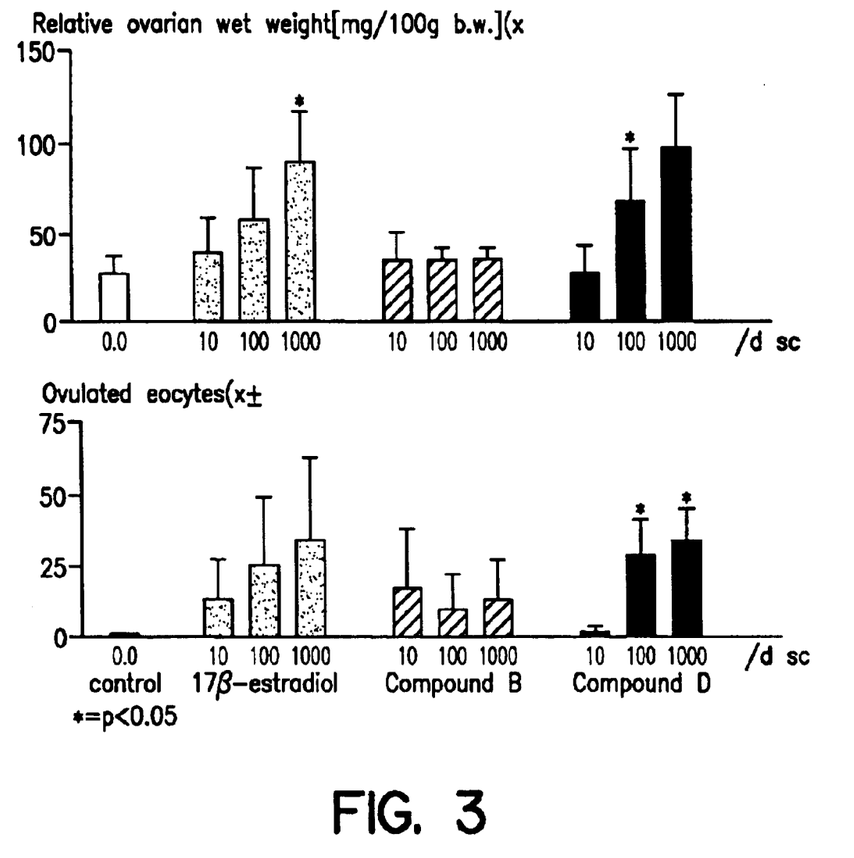
FIG. 3 shows the influence of ERα- and ERβ-ligands on folliculogenesis and ovulation-rate in the Hypex immature Wistar rat.

The results presented in FIG. 3 demonstrate that 17β-estradiol, which is a ligand to ERα as well as to ERβ and the ERβ-specific ligand dose-dependently are able to significantly increase the number of ovulated oocytes as well as ovarian wet weight. In contrast, the ERα-specific ligand was not able to significantly stimulate the number of ovulated oocytes or ovarian growth.

According to the present invention ERβ-selective ligands can be used for production of medicaments for regulating fertility. The ERβ-selective ligands may be used with and without the administration of additional sex steroids for the purposes of the invention.

The use without the addition of a progestin is preferred.

According to one aspect of the invention ERβ-selective agonists can be used for treatment of female infertility to support IVF in connection with in vivo treatment, for treatment of females which are suffering from ovarian infertility (PCO syndrom) and for the treatment of ovarian failure associated with aging ("late fertility").

According to the second aspect of the invention ERβ-selective antagonists can be used for ovarian contraception by inhibiting folliculogenesis, ovulation and preimplantational development of ovulated oocytes. The ERβ-selective antagonists can thus be used to produce oral contraceptives with or without further addition of a progestin.

According to the a further aspect of the invention ERβ-selective antagonists can be used for methods of ovarian contraception by inhibiting folliculogenesis, ovulation and preimplantational development of ovulated oocytes by administering the ERβ-selective antagonist to a female desiring contraception. The ERβ-selective antagonists can administered with or without any further progestin.

By way of inhibition of the folliculogenesis under the treatment with an ERβ-antagonist the lifetime of the follicles is prolonged thus leading to maintenance of the pool of the follicels.

The compounds can be used for the mentioned indications both after oral and parenteral administration.

The amount of a compound with ERβ-agonistic or ERβ-antagonistic activity that is to be administered varies within a wide range and can cover any effective amount. On the basis of the condition that is to be treated or the effect to be achieved and the type of administration, the amount of the compound that is administered can be 0.01 μg/kg-100 mg/kg of body weight, preferably 0.1 μg/kg-10 mg/kg of body weight, per day.

In humans, this corresponds to a dose of 0.8 μg to 8.000 mg, preferably 8 μg to 800 mg, daily.

According to the invention, a dosage unit contains 1.6 μg to 2000 mg of one or more compounds with ERβ-agonistic or ERβ-antagonistic activity.

The compounds with ERβ-agonistic or ERβ-antagonistic activity according to the invention are suitable for the production of pharmaceutical compositions and preparations. The pharmaceutical compositions or pharmaceutical agents contain as active ingredient one or more of the compounds according to the invention or their acid addition salts, optionally mixed with other pharmacologically or pharmaceutically active substances. The production of the pharmaceutical agents is carried out in a known way, whereby the known and commonly used pharmaceutical adjuvants as well as other commonly used vehicles and diluents can be used.

As such vehicles and adjuvants, for example, those are suitable that are recommended or indicated in the following bibliographic references as adjuvants for pharmaceutics, cosmetics and related fields: Ullmans Encyklopädie der technischen Chemie [Ullman's Encyclopedia of Technical Chemistry], Volume 4 (1953), pages 1 to 39; Journal of Pharmaceutical Sciences, Volume 52 (1963), page 918 ff., issued by Czetsch-Lindenwald, Hilfsstoffe für Pharmazie und angrenzende Gabiete [Adjuvants for Pharmaceutics and Related Fields]; Pharm. Ind., Issue 2, 1961, p 72 and ff., Dr. H. P. Fiedler, Lexikon der Hilfsstoffe für Pharmazie, Kosmetik und angrenzende Gebiete [Dictionary of Adjuvants for Pharmaceutics, Cosmetics and Related Fields], Cantor KG, Aulendorf in Württemberg 1971.

The compounds can be administered orally or parenterally, for example intraperitoneally, intramuscularly, subcutaneously or percutaneously. The compounds can also be implanted in the tissue.

For oral administration, capsules, pills, tablets, coated tablets, etc., are suitable, In addition to the active ingredient, the dosage units can contain a pharmaceutically compatible vehicle, such as, for example, starch, sugar, sorbitol, gelatin, lubricant, silicic acid, talc, etc. For parenteral administration, the active ingredients can be dissolved or suspended in a physiologically compatible diluent. As diluents, very often oils with or without the addition of a solubilizer, a surfactant, a suspending agent or an emulsifying agent are used. Examples of oils that are used are olive oil, peanut oil, cottonseed oil, soybean oil, castor oil and sesame oil.

The compounds can also be used in the form of a depot injection or an implant preparation, which can be formulated so that a delayed release of active ingredient is made possible. As inert materials, implants can contain, for example, biodegradable polymers, or synthetic silicones such as, for example, silicone rubber. In addition, for percutaneous administration, the active ingredients can be added to, for example, a patch.

For the production of intravaginal systems (e.g., vaginal rings) or intrauterine systems (e.g., pessaries, coils, IUDs, Mirena®) that are loaded with a compound with ERβ-agonistic or ERβ-antagonistic activity for local administration, various polymers are suitable, such as, for example, silicone polymers, ethylene vinyl acetate, polyethylene or polypropylene. To achieve better bio-availability of the active ingredient, the compounds can also be formulated as cyclodextrin clathrates. For this purpose, the compounds are reacted with α-, β-, or γ-cyclodextrin or derivatives of the latter (PCT/EP95/02656).

According to the invention, the compounds with ERβ-agonistic or ERβ-antagonistic activity can also be encapsulated with liposomes.

The further object of this invention is to provide compounds that have in vitro a dissociation with respect to the binding to estrogen receptor preparations from rat prostates and rat uteri and that exert a contraceptive action in vivo by their preferential action on the ovary without influencing other estrogen-sensitive organs, such as, e.g., the uterus or the liver. These compounds also are to be used for contraception in men as well as for treating benign or malignant proliferative diseases of the ovary.

This object is achieved by the provision of the 17-chloro-D-homosteroids of general formula I in which
R$_1$ means a hydrogen atom or a C$_{1-6}$ alkanoyl radical or benzoyl radical,
R$_2$ means a C$_{1-6}$ alkyl group,
R$_3$ means a hydrogen atom, a C$_{1-6}$ alkyl radical, C$_{1-6}$ alkanoyl radical or benzoylyl radical, and
R$_4$ means a hydrogen atom, a C$_{1-6}$ alkyl radical, a C$_n$F$_{2n+1}$ group, in which n=1, 2 or 3, or a C≡CR$_5$ group, in which R$_5$ is a hydrogen atom, a C$_{1-6}$ alkyl radical or an unsubstituted or substituted phenyl radical.

Especially preferred are

17-Chloro-17aα-ethinyl-17a,18a-dihomo-estra-1,3,5(10),16-tetraene-3,17aβ-diol
17-chloro-17aα-propinyl-17a,18a-dihomo-estra-1,3,5(10),16-tetraene-3,17aβ-diol
17-chloro-13β-ethyl-17aα-methyl-17a,18a-dihomo-estra-1,3,5(10),16-tetraene-3,17aβ-diol
17aβ-acetoxy-17-chloro-17aα-methyl-17a,18a-dihomo-estra-1,3,5(10),16-tetraene-3-ol
17-chloro-17aα-(trifluoromethyl)-17a,18a-dihomo-estra-1,3,5(10),16-tetraene-3,17aβ-diol
17-chloro-17aα-(pentafluoroethyl)-17a,18a-dihomo-estra-1,3,5(10),16-tetraene-3,17aβ-diol
17-chloro-17aα-methyl-17aβ-(methoxy)-17a,18a-dihomo-estra-1,3,5(10),16-tetraene-3-ol
17-chloro-17a-homoestra-1,3,5(10),16-tetraene-3,17aβ-diol
17-chloro-17aα-(trifluoromethyl)-17a-homoestra-1,3,5(10),16-tetraene-3,17aβ-diol
17-chloro-17aα-(pentafluoroethyl)-17a-homoestra-1,3,5(10),16-tetraene-3,17aβ-diol
17-chloro-17aα-methyl-17a-homoestra-1,3,5(10),16-tetraene-3,17aβ-diol 17-chloro-17aα-ethyl-17a-homoestra-1,3,5(10),16-tetraene-3,17aβ-diol
17-chloro-17aα-ethinyl-17a-homoestra-1,3,5(10),16-tetraene-3,17aβ-diol
17-chloro-17aα-propinyl-17a-homoestra-1,3,5(10),16-tetraene-3,17aβ-diol
17-chloro-17aα-(trifluoromethyl)-17a-homoestra-1,3,5(10),16-tetraene-3,17aβ-diol-diacetate
17aβ-acetoxy-17-chloro-17aα-(trifluoromethyl)-17a-homoestra-1,3,5(10),16-tetraene-3-ol
17-chloro-17aβ-methoxy-17aα-(trifluoromethyl)-17a-homoestra-1,3,5(10),16-tetraene-3-ol
17-chloro-(17aα)-21-(4'-methylsulfonylphenyl)-17a,18a-dihomogona-1,3,5(10),16-tetraen-20-yne-3,17aβ-diol
17-chloro-(17aα)-21-(phenyl)-13β-methyl-17a-homogona-1,3,5(10),16-tetraen-20-yne-3,17aβ-diol
17-chloro-(17aα)-21-(4'-cyanophenyl)13β-methyl-17a-homogona-1,3,5(10),16-tetraen-20-yne-3,17aβ-diol
17-chloro-(17aα)-21-(4'-acetylaminophenyl)-13β-methyl-17a-homogona-1,3,5(10),16-tetraen-20-yne-3,17aβ-diol
17-chloro-(17aα)-21-(4'-hydroxyphenyl)-13β-methyl-17a-homogona-1,3,5(10),16-tetraen-20-yne-3,17aβ-diol.

The $C_1$–$C_6$ alkanoyl radical within $R^1$ and $R^3$ is, for example, an acetyl, propionyl, butyryl, isobutyryl, valeryl or pivaloyl radical.

Representatives of the $C_1$–$C_6$ alkyl radicals within $R^1$, $R^2$, $R^3$, $R^4$ and $R^5$ are, for example, methyl, ethyl, propyl, isopropyl, butyl, isobutyl, tert-butyl, pentyl, isopentyl, neopentyl and hexyl.

Perfluorinated alkyl groups $C_nF_{2n+1}$ with n=1,2,3 are trifluoromethyl, pentafluoroethyl and heptafluoropropyl.

As substituents for phenyl radical $R^5$, for example, a methyl-, ethyl-, trifluoromethyl-, pentafluoroethyl-, trifluoromethylthio-, methoxy-, ethoxy-, nitro-, cyano-, halogen- (fluorine, chlorine, bromine, iodine), hydroxy-, amino-, mono($C_{1-8}$ alkyl) or di($C_{1-8}$alkyl)amino, whereby both alkyl groups are identical or different, di(aralkyl)amino, whereby both aralkyl groups are identical or different, can be mentioned.

The compounds of formula I can be prepared by a process characterized in that a 17-chloro-1,3,5(10), 16-tetraene-17-one of general formula II (II)

in which
R₁ means a hydrogen atom, a $C_{1-5}$ alkyl radical, a $C_{1-6}$ alkanoyl radical or a benzoyl radical,
R₂ means $C_{1-6}$ alkyl group,
is convened with a magnesium-organic reagent of general formula BrMg alkyl, BrMg alkenyl or BrMg alkinyl or with acetylene or an alkyl- or aryl-substituted acetylene in the presence of bases such as tert-BuOk or with a lithium-organic compound such as $L_1C_2F_3$, or with a silicon-organic compound such as trifluoromethyl trimethylsilane into a 17aα-substituted compound of general formula III, (III)

in which
R₁ is a hydrogen acorn, a $C_{1-6}$ alkyl radical, a $C_{1-6}$ alkanoyl radical or a benzoyl radical,
R₂ is a $C_{1-6}$ alkyl group,
R₃ is a hydrogen atom, a metal atom or a silyl group, and
R₄ is a hydrogen atom, a $C_{1-6}$ alkyl group, a $C_nF_{2n-1}$ group, in which n=1, 2 or 3, or a C≡CR₅ group, in which R₅ is a hydrogen atom, a $C_{1-6}$ alkyl radical or an unsubstituted or substituted phenyl radical,
whereby in the case of R₅=hydrogen, the free 17aα-ethinyl compound of general formula III is further modified by a SONAGASHIRA reaction to form compounds with $R_5=C_6H_4R_6$, in which R₆ stands for a free or substituted hydroxyl group, amino group, thiol group, sulfamate group, sulfonyl group or a $C_{1-6}$ alkyl group or $C_{6-12}$ aryl group.

In another aspect, the compounds of formula III in which R₁ is a $C_{1-6}$ alkyl radical, are converted by ether cleavage into the free hydroxyl group.

In another aspect, the compounds of formula III in which R₁ is an acyl radical, are converted by ether cleavage into the free hydroxyl groups.

In another aspect, the compounds of formula III, in which R₃ is a hydrogen atom, are converted into ethers or esters.

The new compounds are suitable for inhibiting folliculogenesis and ovulation, for male contraception and for treating benign and malignant proliferative diseases of the ovary. The new compounds are selective antagonists to the estrogen receptor β.

Unlike in the estrogen ethinylestradiol that is commonly used for hormonal contraception or else in the compounds that are to be used for contraception according to WO 00/31112, the compounds of general formula I according to the invention can be used by themselves, i.e., without the additional administration of gestagens for contraception.

As prodrugs, the esters of the compounds of general formula I according to the invention may have advantages compared to the unesterified active ingredients with respect to their method of administration, their type of action, strength and duration of action.

In this patent application, 17-chloro-D-homosteroids are described for contraception, which have in vitro dissociation with respect to binding to estrogen receptor preparations from rat prostates and rat uteri and which have in vivo preferably an inhibition of folliculogenesis and ovulation: these substances have a contraceptive action over a wide dose range without influencing other estrogen-sensitive organs, such as, e.g., the uterus or the liver.

Moreover, these compounds can be used for male contraception and for treatment of benign or malignant proliferative diseases of the ovary.

The invention also relates to pharmaceutical preparations that contain at least one compound of general formula I for the production of pharmaceutical agents, especially for the indications below.

The compounds can be used for the following indications both after oral and parenteral administration.

The novel selective estrogens that are described in this patent can be used as individual components in pharmaceutical preparations or in combination especially with GnRH-antagonists, progesterone receptor antagonists, meso-progestins or gestagens or tissue-selective gestagens.

The substances and the pharmaceutical agents that contain them are especially suitable for ovarian contraception, for the treatment of benign or malignant proliferative diseases of the ovary, such as, e.g., ovarian cancer, and granulosa cell tumors.

In addition, the compounds can be used for treating male fertility disorders and prostatic diseases.

The amount of a compound of general formula I that is to be administered varies within a wide range and can cover any effective amount. On the basis of the condition that is to be treated and the type of administration, the amount of the compound that is administered can be 0.01 μg/kg-100 mg/kg of body weight, preferably 0.04 μg/kg-1 mg/kg of body weight, per day.

In humans, this corresponds to a dose of 0.8 μg to 8 g, preferably 3.2 μg to 80 mg, daily.

According to the invention, a dosage unit contains 1.6 μg to 2000 mg of one or more compounds of general formula I.

The compounds of general formula I are suitable for the production of pharmaceutical compositions and preparations. The pharmaceutical compositions or pharmaceutical agents contain as active ingredients one or more of the compounds according to the invention, optionally mixed with other pharmacologically or pharmaceutically active substances. The production of the pharmaceutical agents is carried out in a known way, whereby the known and commonly used pharmaceutical adjuvants as well as other commonly used vehicles and diluents can be used.

The formulation of the compounds of general formula I can be done in the same manner as described before for the compounds with ERβ-agonistic or ERβ-antagonistic activity.

Methods

Estrogen Receptor Binding Studies

The binding affinity of the new selective estrogens was tested in competitive experiments with use of 3H-estradiol as a ligand to estrogen receptor preparations from rat prostates and rat uteri. The preparation of prostate cytosol and the estrogen receptor test with prostate cytosol was carried out as described by Testas et al. (1981) (Testas, J. et al., 1981, Endocrinology 109:1287–1289).

The preparation of rat uterus cytosol as well as the receptor test with the ER-containing cytosol were basically performed as described by Stack and Gorski, 1985 (Stack, Gorski 1985, Endocrinology 117, 2024–2032) with some modifications as described in Fuhrmann et al. (1995) (Fuhrmann, U. et al. 1995, Contraception 51:45–52).

The substances that are described in this patent have higher binding affinity to the estrogen receptor from rat prostates than to estrogen receptors from rat uteri. In this case, it is assumed that ERβ predominates in the rat prostates over ERα, and ERα predominates in rat uteri over ERβ. Table 1 shows that the ratio of the binding to prostate and uterus receptors qualitatively coincides with the quotient of relative binding affinity (RBA) to human ERβ and ERα of rats (according to Kuiper et al. (1996), Endocrinology 138:863–870) (Table 1).

TABLE 1

| Estrogen | Structure | hERα RBA* | hERβ RBA* | ERβ/ ERα | Rat uterus ER(RBA) | Rat prost. ER(RBA) | prost. ER/ uterus ER |
|---|---|---|---|---|---|---|---|
| Estradiol | | 100 | 100 | 1 | 100 | 100 | 1 |
| Estrone | | 60 | 37 | 0.6 | 3 | 2 | 0.8 |
| 17a-Estradiol | | 58 | 11 | 0.2 | 2.4 | 1.3 | 0.5 |

TABLE 1-continued

| Estrogen | Structure | hERα RBA* | hERβ RBA* | ERβ/ ERα | Rat uterus ER(RBA) | Rat prost. ER(RBA) | prost. ER/ uterus ER |
|---|---|---|---|---|---|---|---|
| Estriol | | 14 | 21 | 1.5 | 4 | 20 | 5 |
| 5-Androstenediol | | 6 | 17 | 3 | 0.1 | 5 | 50 |
| Genisteine | | 5 | 36 | 7 | 0.1 | 10 | 100 |
| Coumestrol | | 94 | 185 | 2 | 1.3 | 24 | 18 |

*Cited from: Kuiper et al. (1996), Endocrinology 138: 863–870

Sample Studies of Contraceptive Action
Study of Early Folliculogenesis:

Immature female rats are hypophysectomized. This day is defined as day 0. From day 1-day 4, subcutaneous and/or oral treatment is carried out with the active substance in combination with 17β-estradiol. The animals were autopsied on day 5. The ovary is removed and analyzed macroscopically, e.g., organ weights, and microscopically, e.g., histological evaluation of the follicles, so-called follicle staging.

Study of Late Folliculogenesis/Ovulation

Immature female rats are hypophysectomized. This day is defined as day 0. From day 1-day 4, subcutaneous and/or oral treatment is carried out with the active substance in combination with 17β-estradiol. On day 5, a subcutaneous injection with PMSG (pregnant mare serum gonadotrophin) is carried out. On day 7, hCG is administered intraperitoneally to trigger ovulation, On day 8, the ovary is removed and analyzed macroscopically (e.g., ovary weight) and/or microscopically (e.g., histological evaluation of the follicles, so-called follicle staging). The tubes are flushed, and checked for the presence of egg cells Study of Ovulation Immature female rats are treated (day 1) subcutaneously with PMSG (pregnant mare serum gonadotrophin) at the age of 23 days. On the same day, as well as 24 and 48 hours later, the animals receive the active substance, administered subcutaneously or orally. 54 hours after the PMSG injection, the animals receive an intraperitoneal injection of hCG to trigger ovulation. Autopsy is carried out 16 hours after the hCG is administered. The tubes are flushed and checked for the presence of egg cells.

Another possibility to detect in vivo the dissociated estrogen action of the substances according to the invention consists in the fact that after a one-time administration of the substances in rats, effects on the expression of 5HT2a-receptor and serotonin transporter protein and mRNA levels in ERβ-rich brain areas can be measured. Compared to the effect on the serotonin receptor and transporter expression, the effect on the LH-secretion is measured. Substances with higher binding to the rat prostate—compared to the rat uterus estrogen receptor—are more potent with respect to increasing the expression of serotonin receptors and transporters, in comparison to their positive effect on the LH release. The density of serotonin receptors and transporters is determined in brain sections using radioactive ligands, and the corresponding mRNA is determined using in situ hybridization. The method is described in the literature: G Fink & B. E. H. Sumner 1996 Nature 383–306; B. E. H. Sumner et al. 1999 Molecular Brain Research, in press.

The compounds of general formula I according to the invention are produced as described in the examples as well as in claims 14 to 16. Additional compounds of general formula I can be obtained by an analogous procedure using reagents that are homologous to the reagents that are described in the examples.

The examples below are used for the explanation of the invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

Example 1

17-Chloro-17a,18a-dihomo-estra-1,3,5(10),16-tetraen-20-yne-3,17aβ-diol 742 mg of 17-chloro-3-methoxy-17a,18a-dihomo-estra-1,3,5(10),16-tetraen-20-yne-17aβ-ol is dissolved in 16 ml of dry dichloromethane and cooled under argon to −78° C. After 2.2 g of tetrabutylammonium iodide and 6 ml of a solution of 1 M boron trichloride in dichloromethane are added, it is stirred for 30 more minutes in a cold bath. The batch is then allowed to come to room temperature and stirred for one more hour. For decomposition, it is cooled to 0° C., the solution is stirred into water and extracted with dichloromethane. After the phase separation, the organic phase is washed with saturated aqueous sodium bicarbonate solution and with water, dried with $Na_2SO_4$, filtered off and concentrated by evaporation under vacuum. The crude product is purified by means of preparative layer chromatography with the mobile solvent mixture of toluene/acetone 20:1. 264 mg of 17-chloro-17aα-ethinyl-17a,18a-dihomo-estra-1,3,5(10)16-tetraene-3,17aβ-diol is obtained.

Melting point: 81 to 88° C. (tert-butyl methyl ether/n-hexane)

$α_D$:−144° ($CHCl_3$)

$^1$H-NMR:

GC/MS: 99.8% F for $M^+1=356$

Production of the Starting Compound

Stage A

3-Methoxy-18a-homoestra-1,3,5(10)-triene-17-one 25.4 g of 3-methoxy-18a-homoestra-1,3,5(10)-triene-17β-ol is dissolved in 500 ml of acetone and cooled to 10° C. Jones reagent is added in drops at 10° C. until a distinct yellow coloring is left. While being cooled with ice, 15 ml of isopropanol is added to decompose the excess reagent, and 1.5 l of water is stirred in, whereby the steroid precipitates out. Crystals are suctioned off, washed neutral with water and dried. The crude product (22.7 g) is purified by recrystallization from ethyl acetate. 17 g of 3-methoxy-18a-homoestra-1,3,5(10)-triene-17-one is obtained.

Stage B

17-Chloro-3-methoxy-17a,18a-dihomo-estra-1,3,5(10),16-tetraene-17a-one 20.3 g of 3-methoxy-18a-homoestra-1,3,5(10)-triene-17-one is dissolved in 400 ml of tetrahydrofuran and cooled under argon to −78° C. Within 30 minutes, 55 ml of a 2 M solution of lithium diisopropylamide in THF/heptane/ethylbenzene is added in drops and stirred for 1.5 more hours. 15.5 ml of chlorotrimethylsilane is now added in drops, and after another 30 minutes of stirring at −78° C., the batch is allowed to come to room temperature. After 2 hours, 300 ml of saturated sodium bicarbonate solution and ethyl acetate are added. After the phase separation, the organic phase is washed with sodium chloride solution, dried on sodium sulfate and concentrated by evaporation under vacuum. The yellow resin (22.7 g) on 17β-trimethylsilyloxy-18a-homoestra-1,3,5(10),16-tetraene-3-methyl ether that is obtained in this way is used as a crude product for the additional reaction. The crude product is dissolved in 350 ml of chloroform and mixed under argon with 60 g of sodium trichloroacetate and 1.5 g of benzyl-triethylammonium chloride and refluxed for 4 hours. For working-up, the reaction solution is cooled and washed in succession twice each with saturated sodium bicarbonate solution, saturated ammonium chloride solution and with saturated sodium chloride solution. It is dried on sodium sulfate, and the solvent is vacuum-evaporated. 30.3 g of a dark brown resin, which is purified by means of flash chromatography and recrystallization from acetone/n-hexane, is obtained.

Yield: 7.8 g of 17-chloro-3-methoxy-17a,18a-dihomoestra-1,3,5(10),16-tetraene-17a-one.

Melting point: 156 to 160° C. (acetonein-hexane)

$α_D$:−44° ($CHCl_3$)

$^1$H-NMR (300 MHz, $CDCl_3$, TMS): 0.71 (t, 3H, H-20), 2.86 (m, 2H, $CH_2$); 3.77 (s, 3H, $OCH_3$), 6.6, 6.71, 7.0 (3H, aromatic-CH), 7.20 (d, 8.4 Hz, H-16).

LC/MS: 345 ($M^++1$) 99.7% F

Literature; i.a., W. Schwede et al., Steroids 59, 176–180 (1994)

Stage C

17-Chloro-13β-ethyl-3-methoxy-18,19-dinor-17a-homo-pregna-1,3-5(10),16-tetraen-20-yne-17aβ-ol 13.8 g of 17-chloro-13β-ethyl-3-methoxy-17a-homo-gona-1,3,5(10),16-tetraene-17a-one is dissolved in 40 ml of THF and cooled under argon to −40° C. Within 30 minutes, 60 ml of a 0.5 M solution of ethinylmagnesium bromide solution in THF is added in drops. Then, the reaction solution is allowed to come to room temperature and stirred for 5.5 more hours. For working-up, it is cooled to −5° C., and 60 ml of aqueous NaCl solution is slowly added in drops, and then 30 ml of dichloromethane is added. After phase separation, it is washed neutral with water, dried with sodium sulfate, filtered off and concentrated by evaporation under vacuum. 1.64 g of brown foam, which is purified by means of flash chromatography with toluene and is recrystallized from acetone, is obtained. Yield: 968 mg of 17-chloro-13β-ethyl-3-methoxy-18,19-dinor-17a-homo-pregna-1,3-5(10),16-tetraen-20-yne)-17aβ-ol.

Melting point: 91 to 93° C. (acetone)

$^1$H-NMR (300 MHz, $CDCl_3$, TMS) 1.02 (t; 3H, $CH_2C\underline{H}_3$), 2.85 (m, 2H, $C\underline{H}_2CH_3$), 3.77 (s, 3H, $OCH_3$), 5.91, 6.62, 7.72 (3H, C-H aromat.), 7.23 (d, 1H, H-16).

LC/MS; 345 ($M^++1$)100% F

Example 2

17-Chloro-13β-methyl-18,19-dinor-21-methyl-17a-homo-pregna-1,3-5(10),16-tetraen-20-yne-3,17aβ-diol Production analogous to Example 1 from 17-chloro-13β-ethyl-3-methoxy-18,19-dinor-21-methyl-17a-homo-pregna-1,3-5 (10),16-tetraen-20-yne-17aβ-ol Melting point: 99 to 104° C. (acetonein-hexane)

$α_D$:−140° ($CHCl_3$)

$^1$H-NMR (400 MHz, $CDCl_3$, TMS): 1.01 (t, 3H, H-20), 1.90 (s, 3H, $C/CCH_3$), 2.52 (s, 1H, OH), 2.81 (m, 2H, $CH_2$), 4.97 (br.S, 1H, OH), 5.85, 6.55, 6.64 (3H, CH-aromat.), 7.17 (d, 8.4 Hz, H-16).

LC/MS: 371 ($M^++1$) 99.2% F

Production of the Starting Compound

The production is carried out analogously to Example 1, Stage C, from 1.38 g of 17-chloro-3-methoxy-17a,18a- dihomoestra-1,3,5(10),16-tetraene-17a-one with 40 ml of a 0.5 M solution of 1-propinylmagnesium bromide in THF. The light yellow foam that accumulates as crude product is purified by flash chromatography and recrystallized from tert-butyl methyl ether/n-hexane. Yield: 1.07 g of 17-chloro-13β-ethyl-3-methoxy-18,19-dinor-21-methyl-17a-homopregna-1,3-5(10),16-tetraen-20-yne-17aβ-ol, which is used directly in the next stage (ether cleavage).

$^1$H-NMR (400 MHz, CDCl$_3$, TMS); 1.01 (t, 3H, H-20), 1.90 (s, 3H, propinyl), 2.51 (s, 1H, OH), 2.84 (m, 2H, CH$_2$), 3.77 (s, 3H, OCH$_3$), 5.85, 6.62, 6.72 (3H, aromat.-CH), 7.23 (d, 8.8 Hz, H-16).

Example 3
17aα-Pentafluoroethyl-17-chloro-17a-homo-estra-1,3,5(10),16tetraene-3,17aβ-diol 2 g of 3-methoxy-17-chloro-17a-homo-estra-1,3,5(10),16-tetraene-17a-one is dissolved in 60 ml of diethyl ether and cooled to −78° C. while being stirred. 4.8 g of pentafluoroethyl iodide is added, then 7.6 ml of a 1.5 m solution of methyllithium-lithium bromide complex in diethyl ether is slowly added in drops. It is stirred for 2 hours at −78° C. and then poured onto 200 ml of saturated sodium bicarbonate solution. It is extracted with ethyl acetate, dried and concentrated by evaporation. 3-Methoxy-17aα-pentafluoroethyl-17-chloro-17a-homo-estra-13,5(10),16-tetraene-17aβ-ol, which is reacted in 50 ml of dichloromethane at −70° C. with 4 g of tetrabutylammonium iodide and 12 ml of 1 M boron trichloride solution in dichloromethane, is obtained. After 1 hour at −70° C., it is allowed to heat to 20° C., and 40 ml of water is added. After extractive working-up, it is chromatographed on silica gel for purification and crystallized from acetone. 17aα-Pentafluoroethyl-17-chloro-17a-homo-estra-1,3,5(10),16-tetraene-3,17aβ-diol is obtained.

$^1$H-NMR (CDCl3): 1.02 (s, 3H, H-18), 6.24 (m, 1H, H-16), 6.56 (d, 1H, J=2.7Hz, H-4), 6.64 (dd, 1H, J=8.2, 2.7 Hz H-2), 7.14 (d, 1H, J=8.6 Hz, H-1)

$^{19}$F-NMR: −78.4 (3F, CF3), −113 (2F, CF2)

Example 4
17aα-Pentafluoroethyl-17-chloro-17a,18a-dihomo-estra-1,3,5(10),16-tetraene-3,17aβ-diol The compound is produced analogously to the above from 3-methoxy-17-chloro-17a,18a-dihomo-estra-1,3,5(10),16-tetraene-17a-one.

$^1$H-NMR (CDCl3): 1.04 (t, 3H, J=7Hz, CH$_2$-CH), 6.27 (m, 1H, H-16), 6.56 (d, 1H, J=2.7 Hz, H-4), 8.64 (dd, 1H, J=8.2, 2.7 Hz, H-2), 7.15 (d, 1H, J=8.6 Hz, H-1)

$^{19}$F-NMR: −78.3 (3F, CF3), −112.9 (2F, CF2)

Example 5
17-Chloro-17aα-(trifluoromethyl)-17a-homoestra-1,3,5(10),16-tetraene-3,17aβ-diol 1.9 g of 17-chloro-17aα-(trifluoromethyl)-17aβ-(trimethylsiloxy)-17a-homoestra-1,3,5(10),16-tetraene-3-ol is dissolved in a Teflon flask in 15 ml of tetrahydrofuran. After 4 ml of hydrofluoric acid (48%) is added, the flask is sealed tightly. It is heated for 25 hours to 50° C.

For working-up, the reaction mixture is added to a solution that consists of 800 ml of 10% ammonium chloride solution with 5 g of calcium gluconate-monohydrate, and it is stirred for 30 minutes at room temperature. By extraction with ethyl acetate and standard working-up (see Example 1), 1.74 g of crude product is isolated, which is purified by means of flash chromatography on MERCK silica gel with a dichloromethane/n-hexane gradient and is recrystallized from acetone/n-hexane. Yield: 1.36 g of 17-chloro-17aα-(trifluoromethyl) 17a-homoestra-1,3,5(10),16-tetraene-3,17aβ-diol Melting point: 187 to 192° C. (acetone/n-hexane)

α$_D$:−15° (CHCl$_3$)

$^1$H-NMR (300 MHz, CDCl$_3$, TMS): 1.03 (s, 3H, H-18), 2.81 (m, 2H, CH$_2$), 3.04 (s, 1H, OH), 4.97 (s, 1 H, OH), 6.23 (t, 1H, H-16), 6.55 (d, 1H, C-4 arom. CH), 6.63 (dd, 1H, C-2 arom.CH), 7.14 (d, 8.2 Hz, C-1 arom. CH).

HPLC: 98.9% F at 280 nm

GC/MS: 387 (M$^+$+1) 100% F

Production of the Starting Compounds

Stage A

17-Chloro-3-methoxy-17a-homoestra-1,3,5(10,16-tetraene-17-one 30 g of 3-methoxy-estra-1,3,5(10)-triene-17-one is converted as under Example 1, Stage B, with lithium diisopropylamide and trimethylchlorosilane into 17β-trimethylsilyloxy-estra-1,3,5(19,16-tetraene-3-methyl ether. The crude product that is obtained in this case (44.6 g) is used directly in the next stage.

$^1$H-NMR (300 MHz, CDCl$_3$, TMS): 0.21 (s, 9H, Si(CH$_3$)$_3$, 0.86 (s, 3H, H-18), 2.84 (m, 2H, CH$_2$), 3.78 (s, 3H, OCH$_3$), 4.52 (t, 1H, H-1), 6.23 (t, 1H, H-16), 6.64 (d, 1H, C-4 arom. CH), 6.70 (dd, 1H, C-2 arom. CH), 7.20 (d, 8.2 Hz, C-1 arom. CH).

125 g of sodium trichloroacetate and 2.9 g of benzyltriethylammonium chloride are added under argon to 37.6 g of 17β-trimethylsilyloxy-estra, 1,3,5(19,16-tetraene-3-methyl ether in 540 ml of chloroform, and the mixture is refluxed for 6 hours. The batch is decomposed by adding aqueous sodium bicarbonate solution and worked up as usual. 52.3 g of a dark brown resin, which is purified by means of flash chromatography with a toluene/dichloromethane gradient and by recrystallization from acetone/n-hexane, is isolated. Yield: 14.2 g of 17-chloro-3-methoxy-17a-homoestra-1,3,5(10),16-tetraene-17-one.

Melting point: 166 to 169° C. (acetone)

α$_D$:−18° (CHCl$_3$)

$^1$H-NMR (300 MHz, CDCl$_3$, TMS): 1.07 (s, 3H, H-18), 2.84 (m, 2H, CH$_2$), 3.76 (s, 3, H, OCH$_3$), 6.61 (d, 1H, H-16), 6.72 (d, 1H, C-4 arom.CH), 7.05 (dd, 1H, C-2 arom.CH), 7.20 (d, 6.6 Hz, C-1 arom. CH).

HPLC: 98.4 F % at 220 nm

Stage B

17-Chloro-17aα-(trifluoromethyl)-17aβ-(trimethylsiloxy)-17a-homoestra-1,3,5(10),16-tetraene-3-methyl ether 1 g of 17-chloro-3-methoxy-17a-homoestra-1,3,5(10),16-tetraene-17-one is dissolved in 30 ml of absolute THF, mixed with 1 g of molecular sieve 3A and stirred for 30 minutes under argon. It is cooled to 0° C., 1.5 ml of trifluoromethyltrimethylsilane is added in drops, and it is stirred for 10 more minutes. The reaction solution is decomposed by adding 10 ml of 1N HCl. After working-up, 1.05 g of 17-chloro-17aα-(trifluoromethyl)-17aβ-(trimethylsiloxy)-17a-homoestra-1,3,5(10),16-tetraene-3-methyl ether is obtained.

Melting point: 118 to 120° C. (MeOH)

α$_D$:−4° (CHCl$_3$)

$^1$H-NMR (300 MHz, CDCl$_3$, TMS): 0.24 [s, 9H, si(CH$_3$)$_3$], 0.96 (s, 3H, H-18), 2.86 (m, 2H, CH$_2$), 3 78 (s, 3H, OCH$_3$), 6.19 (t, 1H, H-16), 6.63 (d, 1H, C-4 arom. CH), 6.74 (dd, 1H, C-2 arom. CH), 7.21 (d, 6.6 Hz, C-1 arom. CH).

HPLC: 98.7 F % at 278 nm, LC/MS: 471 (M$^+$+1) 99.7% F

Lit.: Krishnamurti Bellew Prakash J. Org. Chem. 56, 984 (1991)

Stage C
17-Chloro-17aα-(trifluoromethyl)-17aβ-(trimethylsiloxy)-17a-homoestra-1,3,5(10),16-tetraene-3-ol 3 g of 17-chloro-17aα-(trifluoromethyl)-17aβ-(trimethylsiloxy)-17a-homoestra-1,3,5(10),16-tetraene-3-methyl ether is dissolved in 80 ml of dry toluene, cooled to −5° C., and mixed with 9 ml of diisobutylaluminum hydride (1 M toluene solution). It is allowed to come to room temperature and then heated for 12 hours to boiling temperature. Then, it is cooled to −20° C., 14 ml of ethanol (95%), then 14 ml of HCl (conc.) and 32 ml of water are added in drops, extracted with ethyl acetate, the organic phase is washed neutral, dried on sodium sulfate, and the filtered solution is concentrated by evaporation under vacuum. 3.1 g of a light-colored foam, which is purified by flash chromatography and recrystallized from methanol, is obtained.

Melting point; 158 to 161° C. (MeOH)
$\alpha_D$:−1° (CHCl$_3$)
$^1$H-NMR (300 MHz, CDCl$_3$, TMS): 0.24 [s 9H, Si(CH$_3$)$_3$], 0.96 (s, 3H, H-18), 2.82 (m, 2H, CH$_2$), 4.63 (s, 1H, OH), 6.19 (t, 1H, J=3.3 Hz, H-16), 6.56 (d, 1H, J=2.7 Hz, C-4 arom. CH), 6.64 (dd, 1H, J=2.7 and 8.4 Hz, C-2 arom. CH), 7.16 (d, 1 H, J=8.4 Hz, C-1 CH-arom.).
HPLC: 99.9 F % at 278 nm, GC/MS: 459 (M$^+$+1) 99.7% F Example 6
17-Chloro-17aα-methyl-17a-homoestra-1,3,5(10),16-tetraene-3,17aβ-diol 464 mg of 17-chloro-3-methoxy-17aα-methyl-17a-homoestra-1,3,5(10),16-tetraene-17aβ-ol is cleaved in 20 ml of toluene according to Example 4, Stage C, with diisobutylaluminum hydride. 520 mg of crude product is obtained as light-colored crystals, which are purified by means of preparative layer chromatography with the mobile solvent mixture of toluene/methanol 5:1. After recrystallization from acetone/n-hexane and from methanol, 192 mg of 17-chloro-17aα-methyl-17a-homoestra-1,3,5(10),16-tetraene-3,17aβ-diol is obtained.

Melting point: 207 to 221° C. (MeOH)
$\alpha_D$:−33° (CHCl$_3$)
$^1$H-NMR (300 MHz, CDCl$_3$, TMS): 1.01 (s, 3H, H-18), 1.40 (s, 3H, H-20), 2.80 (m, 2H, CH$_2$), 5.37 (s, 1H, OH), 5.80 (m, 1H, H-16), 6.57 (d, 1H, J=2.7 Hz, C-4 arom.CH), 6.64 (dd, 1H, J=2.7 and 8.4 Hz, C-2 arom. CH), 7.17 (d, 1H, J=8.4 Hz, C-1 arom. CH).
HPLC: 98.4 F % at 281 nm, GC/MS; 333 (M$^+$+1) 99.1% F Production of the Starting Compound
Stage A
17-Chloro-3-methoxy-17aα-methyl-17a-homoestra-1,3,5(10),16-tetraene-17aβ-ol 660 mg of 17-chloro-3-methoxy-17a-homoestra-1,3,5(10),16-tetraene-17a-one is dissolved in 20 ml of dry tetrahydrofuran and cooled under argon to −40° C. Then, 5 ml of a 3 M solution of methylmagnesium bromide in diethyl ether is added in drops. After 5 minutes of stirring in a cold bath, the batch is allowed to come to room temperature. After another 1.5 hours of reaction time, a complete reaction is achieved. The batch is cooled to 0° C. 20 ml of aqueous saturated ammonium chloride solution is slowly added in drops and stirred for 15 minutes. After dichloromethane is added, the phases are separated, and the aqueous phase is subsequently re-extracted. The organic phase is washed neutral, dried with sodium sulfate and vacuum-evaporated. 705 mg of 17-chloro-3-methoxy-17aα-methyl-17a-homoestra-1,3,5(10),16-tetraene-17aβ-ol is obtained as light-colored foam, which is purified by means of preparative layer chromatography Yield: 380 mg of light-colored crystals.

Melting point: 136 to 138° C. (n-hexane)
$\alpha_D$:−37° (CHCl$_3$)
$^1$H-NMR: 1.01 (s, 3H, H-18), 1.40 (s, 3H, H-19), 1.91 (s, 1H, OH), 3.78 (s, 3H, OCH$_3$), 5.8 (m, H, H-16); 6.63, 6.73, 7.22 (3H, aromat. H)
HPLC: 92.8% F at 280 nm, LC/MS: M$^+$+1=347 (98.9% F)

Example 7
17-Chloro-17aα-ethinyl-17a-homoestra-1,3,5(10),16-tetraene-3,17aβ-diol 1.35 g of 17-chloro-17aα-ethynyl-3-methoxy-17a-homoestra-1,3,5(10),16-tetraene-17aβ-ol is reacted in 15 ml of dichloromethane with tetrabutylammonium iodide and 12 ml of boron trichloride (1 M in dichloromethane) according to Example 1. 4.4 g of crude product is obtained as a brown resin, which is purified by means of flash chromatography on toluere/acetone gradients and is recrystallized from ether/n-hexane. The 1.23 g of purified.

594 mg of 17-chloro-17aα-ethynyl-17a-homoestra-1,3,5(10),16-tetraene-3,17aβ-diol is obtained.

Melting point: 172 to 177° C. (diethyl ether/n-hexane)
$\alpha_D$:−131° (CHCl$_3$)
$^1$H-NMR (300 MHz, DMSO, TMS): 0.84 (s, 3H, H-18), 2.50 (m, 2H, CH$_2$), 2.69 (s, 1H C/CH), 5.82 (d, 1H, H-16), 6.43 (d, 1H, C-4 arom.CH), 6.51 (dd, 1H, C-2 arom. CH), 7.07 (d, 6.6 Hz, C-1 arom. CH), 9.00 (s, 1H, OH)
HPLC: 99.3% F at 280 nm, GC/MS: M$^+$=343 (M$^+$+1) 98.9% F Example 8
17-Chloro-17aα-propinyl-17a-homoestra-1,3,5(10),16-tetraene-3,17aβ-diol 835 mg of 17-chloro-3-methoxy-17aα-propinyl-17a-homoestra-1,3,5(10),16-tetraene-3,17aβ-ol is cleaved in 20 ml of toluene under argon with 4 ml of diisobutylaluminum hydride (DIBAH solution 95% in toluene) according to Example 1, Stage C. After standard working-up, 800 mg of light-colored foam on 17-chloro-17aα-propinyl-17a-homoestra-1,3,5(10),16-tetraene-3,17aβ-diol, which is purified by means of preparative layer chromatography with a toluene/dichloromethane mixture and is recrystallized from ketone, is obtained. Yield. 137 mg Melting point: 101 to 104° C. (acetone)
$\alpha_D$:−144° (CHCl$_3$)
$^1$H-NMR (300 MHz, DMSO, TMS): 0.97 (s, 3H, H-18), 2.56 (s, 1H, C/CCH$_3$), 5.15 (s, 1H, OH), 5.84 (d, 1H, H-16), 6.56 (d, 1H, C-4 arom. CH), 6.65 (dd, 1 H, C-2 arom CH), 7.17 (d, 6.6 Hz, C-1 arom. CH).
HPLC: 97.5% F at 278 nm, GC/MS: M$^+$=357 (M$^+$+1) 99.0% F Production of the Starting Compound
Stage A
17-Chloro-3-methoxy-17aα-propinyl-17a-homoestra-1,3,5(10),16-tetraene-17aβ-ol 660 mg of 17-chloro-3-methoxy-17a-homoestra-1,3,5(10),16-tetraene-17a-one is reacted in 20 ml of dry tetrahydrofuran at −40° C. according to Example 7 with 30 ml of a 0.5 M solution of propinylmagnesium bromide in tetrahydrofuran, and it is worked up as usual. 835 mg of 17-chloro-3-methoxy-17aα-propinyl-17a-homoestra-1,3,5(10),16-tetraene-17aβ-ol is obtained as a light brown foam, which is purified by chromatography.

Melting point: 157 to 162° C. (tert-butyl methyl ether)
$\alpha_D$:−153° (CHCl$_3$)

$^1$H-NMR (300 MHz, CDCl$_3$, TMS): 0.97 (s, 3H, H-18), 1.91 (s, 1H, C/CCH$_3$), 3.78 (s, 3H, OCH$_3$), 5.84 (d, 1H, H-16), 6.62 (d, 1H, C-4 arom. CH), 6.73 (dd, 1H, C-2 arom, CH), 7.23 (d, 6.6 Hz, C-1 arom. CH).

HPLC: 94.3% F at 280 nm, LC/MS 371 (M$^+$+1) 93.6% F

Example 9

17-Chloro-(17aα),21-(4'-methylsulfonylphenyl)-17a-homogona-1,3,5(10),16-tetraen-20-yne-3,17aβ-diol 346 mg of 4-bromophenylmethylsulfone, 5 mg of palladium(II) chloride, 7.3 mg of triphenylphosphine and 2.7 mg of copper(I) iodide in 14 ml of tetrahydrofuran and 7 ml of triethylamine are stirred at room temperature and heated until the boiling point is reached. 480 mg of 17-chloro-17aα-ethinyl-17a-homoestra-1,3,5(10),16-tetraene-17aβ-diol in 14 ml of tetrahydrofuran is added. After 12 hours, the solution is poured into ice water, extracted with dichloromethane, treated with 2N HCl and then washed neutral with water, dried with sodium sulfate, filtered and concentrated by evaporation. 830 mg of crude product, which is purified by preparative layer chromatography, is obtained. 154 mg of 17-chloro-(17aα), 21-(4'-methylsulfonylphenyl)-17a-homogona-1,3,5(10),16-tetraen-20-yne-3,17aβ-diol is obtained as a foam.

$^1$H-NMR (300 MHz, CDCl$_3$, TMS): 0.92 (s, 3H, H-18), 3.22, 3.34 (s, 3H, CH$_3$), 5.92 (d, g 1H, H-16), 6.11 (s, 1H, OH), 6.44 (d, 1H, C-4 arom. CH), 6.52 (dd, 1H, C-2 arom. CH), 7.08 (d, 6.6 Hz, C-1 arom. CH), 7.69 and 7.90 (d, 2H, HC-arom. each), 9.00 (s, 1H, OH).

HPLC; 94.3% F at 280 nm, LC/MS: 497 (M$^+$+1) 98.9% F

The entire disclosures of all applications, patents and publications, cited herein and of corresponding German application No. 101 51 365.8, filed Oct. 17, 2001, and U.S. Provisional Applications Serial Nos. 60/271,409, filed Feb. 27, 2001; 60/329,736 filed Oct. 18, 2001 and 60/331,530 filed Nov. 19, 2001 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for regulating fertility with or without an additional follicular sex steroid comprising administering to a patient in need thereof a therapeutically effective amount of a 17-Chloro-D homosteroid of formula I (I)

in which

R$_1$ is a hydrogen atom or a C$_{1-6}$ alkanoyl radical or a benzoyl radical,

R$_2$ is a C$_1$ alkyl group,

R$_3$ is a hydrogen atom, a C$_{1-6}$ alkyl radical, a C$_{1-6}$ alkanoyl radical or a benzoylyl radical, and R$_4$ is a hydrogen atom, a C$_{1-6}$ alkyl radical, a C$_2$F$_{3n+}$ group, in which n=1, 2 or 3, or a C=CR$_5$ group, in which R$_5$ is a hydrogen atom, a C$_{1-6}$ alkyl radical or an unsubstituted or substituted phenyl radical.

2. The method according to claim 1, wherein a therapeutically effective amount of a 17-Chloro-D homosteroid of formula I is administered for the treatment of female infertility.

3. The method according to claim 2 in connection wish in vitro fertilization.

4. The method according to claim 2, wherein said female infertility is ovarian infertility.

5. The method according to claim 2, in connection with an in viva treatment.

6. A method for treating ovarian failure associated with aging comprising administering to a patient in need thereof a therapeutically effective amount of a 17-Chloro-D homosteroid of formula I (I)

in which

R$_1$ is a hydrogen atom or a C$_{1-6}$ alkanoyl radical or a benzoyl radical,

R$_2$ is a C$_{1-6}$ alkyl group,

R$_3$ is a hydrogen atom, a C$_{1-6}$ alkyl radical, a C$_{1-6}$ alkanoyl radical or a benzoylyl radical, and R$_4$ is a hydrogen atom, a C$_{1-6}$ alkyl radical, a C$_2$F$_{2n+}$ group, in which n=1=2 or 3, or a C=CR$_5$ group, in which R$_5$ is a hydrogen atom, a C$_{1-6}$ alkyl radical or an unsubstituted or substituted phenyl radical.

7. The method according to claim 1, wherein a therapeutically effective amount of a 17-Chloro-D homosteroid of formula I is administered for ovarian contraception.

8. The method according to claim 7, wherein said method inhibits folliculogenesis.

9. The method according so claim 7, wherein said method inhibits ovulation.

10. The method according to claim 7, wherein said method inhibits preimplantational development of ovulated oocytes.

11. A 17-Chloro-D homosteroid of formula I (I)

in which

R$_1$ is a hydrogen atom or a C$_{1-6}$ alkanoyl radical or a benzoyl radical,

R$_2$ is a C$_{1-6}$ alkyl group, $R_3$ is a hydrogen atom, a $C_{1-6}$ alkyl radical, a $C_{1-6}$ alkanoyl radical or a benzoylyl radical, and R4 is a hydrogen atom, a $C_{1-6}$ alkyl radical, a $C_nF_{2n+1}$ group, in which n=1, 2 or 3, or a C>$CR_5$ group, in which $R_5$ is a hydrogen atom, a $C_{1-6}$ alkyl radical or an unsubstituted or substituted phenyl radical.

12. A method for regulating fertility without additional use of a follicular sex steroid comprising administering to a patient in need thereof a pharmaceutical composition comprising a 17-Chloro-D homosteroid of formula I according to claim 11, without the administering of a follicular sex steroid.

13. A compound of formula I according to claim 11, which is

17-Chloro-17aα-ethinyl-17a,18a-dihomo-estra-1,3,5(10), 16-tetraene-3,17aβ-diol 17-chloro-17aβ-propinyl-17a,18a-dihomo-estra-1,3,5(10), 16-tetraene-3,17aβ-diol 17-chloro-13β-ethyl-17aα-methyl-17a,18a-dihomo-estra-1, 3,5(10), 16-tetraene-3,17aβ-diol 17aβ-acetoxy-17-chloro-17aα-methyl-17a,18a-dihomo-estra-1,3,5(10),16-tetraene-3-ol 17-chloro-17aα-(trifluoromethyl)-17a,18a-dihomo-estra-1, 3,5(10), 16-tetraene-dial 17-chloro-17aβ-(pentafluoroethyl)-7a, 18a-dihomo-estra-1, 3,5(10), 16-tetrene-3,17aβ-diol 17-chloro-17aα-methyl-17aα-(methoxy)17a,18a-dihomo-estra-1,3,5(10), 16-tetraene-3-ol 17-chloro-17a-homoestra-1,3,5(10), 16-tetraene-3,17aβ-diol 17-chloro-17aα-(trifluoromethyl)17a-homoestra-1,3,5(10), 16-tetraene-3,17aβ-diol 17-chloro-17aα-(pentafluoroethyl)-17 a-homoestra-1,3,5 (10), 16-tetraene-3,17aα-diol 17-chloro-17aα-methyl-17a-homoestra-1,3,5(10), 16-tetraene-3,17aβ-diol 17-chloro-17aα-ethyl-17a-homoestra-1,3,5(10), 16-tetraene-3,17aβ-diol 17-chloro-17aα-ethinyl-17a-homoestra-1,3,5(10), 16-tetraene-3,17aβ-diol 17-chloro-17aα-propinyl-17a-homoestra-1,3,5(10), 16-tetraene-3,17aβ-diol 17-chloro-17aα-(trifluoromethyl)-17a-homoestra-1,3,5(10), 16-tetraene-3,17aβdiol-diacetate 17aβ-acetoxy-17chloro-17aβ-(trifluoromethyl)-17a-homoestra-1,3,5(10), 16-tetraene-3-ol 17-chloro-17aβ-methoxy-17aα(trifluoromethyl)-17a-homoestra-1,3,5(10), 16-tetraene-3-ol 17-chloro-(17aα)-21-(4'-methysulfonylphenyl)-17a,18a-dihomogona-1,3,5(10),16-tetraen-20-yne-3,17aβ-diol

17-chloro-(17,aα)-21-(phenyl)13β-methyl-17a-homogona-1,3,5(10), 16-tetraene-20-yne-3,17aβ-diol 17-chloro-(17aβ)21-(4-cyanophenyl)13β-methyl-17a-homogona-1,3,5(10), 16-tetraene-20-yne-3,17aβ-diol

17-chloro-(17aα)-21-(4'-acetylaminophenyl)-13β-methyl-17a-homogona-1,3,5(10), 16-tetraene-20-yne-3,17aβ-diol or 17-chloro-(17aβ)-21-(4'-hydroxyphenyl)-13B-methyl-17a-homogona-1,3,5(10), 16-tetraene-20-yne-3,17aβ-diol.

14. A process for the production of a 17-chloro-D-homosteroid of the formula I according to claim 11, comprising converting a 17-chloro-1,3,5(10), 16-tetraene-17-one of formula II in which $R_1$ is a hydrogen atom, a $C_{1-6}$ alkyl radical, a $C_{1-6}$ alkanoyl radical or a benzoyl radical, $R_2$ is $C_{1-6}$ alkyl group, with a magnesium-organic reagent of general formula BrMg alkyl, BrMg alkenyl or BrMg alkinyl or with acetylene or an alkyl- or aryl-substituted acetylene in the presence of a base, or with a lithium-organic compound or with a silicon-organic compound into a 17aα-substituted compound of formula III, in which $R_1$ is a hydrogen atom, a $C_{1-6}$ alkyl radical, a $C_{1-6}$ alkanoyl radical or a benzoyl radical, $R_2$ is a $C_{1-6}$ alkyl group, $R_3$ is a hydrogen atom, a metal atom or a silyl group, and $R_4$ is a hydrogen atom, a $C_{1-6}$ alkyl group, a $C_{1-6}$ group, in which n=1, 2 or 3, or a C=$CR_5$ group, in which $R_5$ is a hydrogen atom, a $C_{1-6}$ alkyl radical or an unsubstituted or substituted phenyl radical, wherein in the case of $R_5$=hydrogen, the free 17aα-ethinyl compound of general formula III is further modified by a SONAOASHIRA reaction to form compounds with $R_5$=$C_6H_4R_6$, in which $R_6$ stands for a free or substituted hydroxyl group, amino group, thiol group, sulfamate group, sulfonyl group or a $C_{1-6}$ alkyl group or a $C_{6-12}$ aryl group.

15. The process according to claim 14, wherein said compound of formula III in which $R_1$ is a $C_{1-6}$ alkyl radical, is converted by ether cleavage into a free hydroxyl group.

16. The process according to claim 14, wherein said compound of formula III, in which $R_1$ is convened by either cleavage into a free hydroxyl group.

17. The process according to claim 14, wherein said compound of formula III in which $R_3$ is a hydrogen atom, is convened into ethers or esters.

18. The process according to claim 14, wherein said base is tert-BuOK.

19. The process according to claim 14, wherein said lithium organic compound is $LiC_2F_5$.

20. The process according to claim 14, wherein said silicon-organic compound is trifluoromethyl trimethylsilane.

21. A method for contraception in women comprising administering to a woman in need thereof a therapeutically effective amount of a compound of formula I according to claim 11.

22. A method for contraception in men comprising administering to a man in need thereof a therapeutically effective amount of a compound of formula I according to claim 11.

23. A method for treating benign or malignant proliferative diseases of the ovary comprising administering to a patient in need thereof a therapeutically effective amount of a compound of formula I according to claim 11.

24. The method of claim 23, wherein said malignant proliferative disease is ovarian cancer.

25. The method of claim 23, wherein said malignant proliferative disease is a granulosa cell tumor.

26. A pharmaceutical composition comprising at least one compound according to claim 11, as well as a pharmaceutically comparable vehicle.

27. A pharmaceutical composition according to claim 26, further comprising a GnRH antagonist, a progesterone receptor antagonist, a mesoprogestin, a gestagen or a tissue-selective gestagen.

* * * * *

UNITED STATES PATENT AND TRADEMARK OFFICE
CERTIFICATE OF CORRECTION

PATENT NO. : 6,794,409 B2
DATED : September 21, 2004
INVENTOR(S) : Hegele-Hartung et al.

It is certified that error appears in the above-identified patent and that said Letters Patent is hereby corrected as shown below:

Column 21,
Line 65, reads "$C_1$" should read -- $C_{1-6}$ --.

Column 22,
Line 1, reads "$C_2F_{3n+}$" should read -- $C_nF_{2n+1}$ --.
Line 9, reads "wish" should read -- with --.
Line 37, reads "$C_2F_{2n+}$" should read -- $C_nF_{2n+1}$ --.
Line 46, reads "so" should read -- to --.

Column 23,
Line 4, reads "$C>C_{R5}$" should read -- $C\equiv C_{R5}$ --.
Line 19, reads "17-chloro-17αβ-propinyl-17a," should read -- 17-chloro-l7αα-propinyl-17a, --
Line 27, reads "16-tetraene-dial" should read -- 16-tetraene-3, 17αβ-diol --.
Line 28, reads "17-chloro-17αβ-(pentafluoroethyl)-7a," should read -- 17-chloro-l7αα-(pentafluoroethyl)-17a, --.
Line 30, reads "17-chloro-l7aα-methyl-17aα-(methoxy)17a," should read -- 17-chloro-17aα-methyl-17aβ-(methoxy)17a, --.
Line 38, reads "16-tetraene-3,17aα-diol" should read -- 16-tetraene-3,17αβ-diol --.
Line 49, reads "17αβ-acetoxy-17chloro-17aβ-(trifluoromethyl)-17a-" should read -- 17aβ-acetoxy-17chloro-l7aα-(trifluoromethyl)-17a- --.
Line 54, reads "17chloro-(17aα)-21-(4'-methysulfonylphenyl)-17a,18a-" should read -- 17-chloro-(17aα)-21-(4'-methylsulfonylphenyl)-17a,18a- --.
Line 58, reads "17-chloro-(17aβ)21-" should read -- 17-chloro-(17aα)21- --.
Line 64, reads "17chloro-(17aβ)-21-(4'hydroxyphenyl-13B-methyl-17a-" should read -- 17-chloro-(17aα)-21-(4'hydroxyphenyl)-13β-methyl-17a- --.

Column 24,
Line 52, reads "a $C_{1-6}$ group" should read -- a $C_nF_{2n+1}$ group --.
Line 66, reads "either" should read -- ether --.

UNITED STATES PATENT AND TRADEMARK OFFICE
CERTIFICATE OF CORRECTION

PATENT NO. : 6,794,409 B2
DATED : September 21, 2004
INVENTOR(S) : Hegele-Hartung et al.

It is certified that error appears in the above-identified patent and that said Letters Patent is hereby corrected as shown below:

Column 26,
Line 10, reads "comparable" should read -- compatible --.

Signed and Sealed this

Fifth Day of July, 2005

JON W. DUDAS
*Director of the United States Patent and Trademark Office*